United States Patent [19]

Kazmaier et al.

[11] Patent Number: 4,552,822

[45] Date of Patent: Nov. 12, 1985

[54] PHOTOCONDUCTIVE DEVICES WITH HYDROXY CONTAINING SQUARAINE COMPOSITIONS

[75] Inventors: Peter M. Kazmaier; Guiseppa Baranyi; Cheng-kuo Hsiao; Richard A. Burt, all of Mississauga, Canada

[73] Assignee: Xerox Corporation, Stamford, Conn.

[21] Appl. No.: 558,246

[22] Filed: Dec. 5, 1983

[51] Int. Cl.[4] .......................... G03G 5/04; G03G 5/14; C07C 87/50

[52] U.S. Cl. .......................................... 430/59; 430/57; 430/73; 430/74; 430/95; 564/307

[58] Field of Search ........................ 430/57, 58, 59, 73, 430/74, 83; 564/307

[56] References Cited

U.S. PATENT DOCUMENTS

| | | | |
|---|---|---|---|
| 4,378,415 | 3/1983 | Chu | 430/59 X |
| 4,415,639 | 11/1983 | Horgan | 430/59 X |
| 4,481,270 | 11/1984 | Kubota et al. | 430/83 X |

FOREIGN PATENT DOCUMENTS

| | | | |
|---|---|---|---|
| 2707086 | 8/1977 | Fed. Rep. of Germany | 430/83 |
| 57-144558 | 9/1982 | Japan | 430/59 |

*Primary Examiner*—Roland E. Martin
*Attorney, Agent, or Firm*—E. O. Palazzo

[57] ABSTRACT

Photoresponsive devices, including layered photoresponsive devices comprised of a photoconductive layer of squaraine compositions of the following formula:

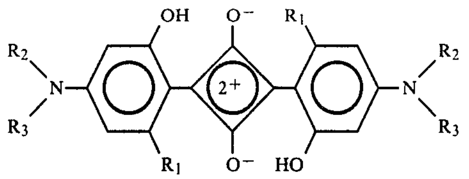

wherein $R_1$, $R_2$, and $R_3$ are independently selected from the group consisting of alkyl substitutents and aryl substituents.

61 Claims, 8 Drawing Figures

PHOTOCONDUCTIVE DEVICES WITH HYDROXY CONTAINING SQUARAINE COMPOSITIONS

BACKGROUND OF THE INVENTION

This invention is generally directed to novel squaraine compositions, and the incorporation of these compositions into layered photoresponsive devices. Thus, in one embodiment, the present invention envisions the use of novel squaraine compositions of matter as organic photoconductive materials in layered photoresponsive devices, especially those devices containing hole transport layers. In one important feature of the present invention, the sensitivity of the layered photoresponsive devices can be varied or enhanced allowing these devices to be capable of being responsive to visible light, and infrared illumination needed for laser printing. Accordingly, layered photoresponsive devices containing the novel squaraine compositions of the present invention can in one embodiment function so as to enhance or reduce the intrinsic properties of a charge carrier photogenerating material contained therein, in the infrared and/or visible region of the spectrum, thereby allowing these devices to be sensitive to either visible light, and/or infrared wavelengths. Moreover, there is provided in accordance with the present invention novel processes for preparing the squaraine compositions illustrated.

Numerous different xerographic photoconductive members are known including, for example, a homogeneous layer of a single material such as vitreous selenium, or a composite layered device, containing a dispersion of a photoconductive composition. An example of one type of composite xerographic photoconductive member is described for example, in U.S. Pat. No. 3,121,006, wherein there is disclosed finely divided particles of a photoconductive inorganic compound dispersed in an electrically insulating organic resin binder. The binder materials disclosed in this patent comprise a material which is incapable of transporting for any significant distance injected charge carriers generated by the photoconductive particles. Accordingly, as a result, the photoconductive particles must be in a substantially contiguous particle-to-particle contact throughout the layer for the purpose of permitting charge dissipation required for a cyclic operation. Thus, with the uniform dispersion of photoconductive particles described, a relatively high volume concentration of photoconductor material, about 50 percent by volume, is usually necessary in order to obtain sufficient photoconductor particle-to-particle contact for rapid discharge. This high photoconductive loading can result in destroying the physical continuity of the resinous binder, thus significantly reducing the mechanical properties thereof. Illustrative examples of specific binder materials disclosed in the '006 patent include, for example, polycarbonate resins, polyester resins, polyamide resins, and the like.

There are also known photoreceptor materials comprised of inorganic or organic materials wherein the charge carrier generating, and charge carrier transport functions, are accomplished by discrete contiguous layers. Additionally, layered photoreceptor materials are disclosed in the prior art which include an overcoating layer of an electrically insulating polymeric material. However, the art of xerography continues to advance and more stringent demands need to be met by the copying apparatus in order to increase performance standards, and to obtain higher quality images. Also, there is desired layered photoresponsive devices which are responsive to visible light, and/or infrared illumination needed for laser printing.

Recently, there have been disclosed other layered photoresponsive devices including those comprised of separate generating layers, and transport layers as described in U.S. Pat. No. 4,265,990, and overcoated photoresponsive materials containing a hole injecting layer, overcoated with a hole transport layer, followed by an overcoating of a photogenerating layer, and a top coating of an insulating organic resin, reference U.S. Pat. No. 4,251,612. Examples of photogenerating layers disclosed in these patents include trigonal selenium and phthalocyanines, while examples of transport layers include certain diamines as mentioned herein. The disclosures of each of these patents, namely, U.S. Pat. Nos. 4,265,990 and 4,251,612, are totally incorporated herein by reference.

Many other patents are in existence describing photoresponsive devices including layered devices containing generating substances, such as U.S. Pat. No. 3,041,167, which discloses an overcoated imaging member containing a conductive substrate, a photoconductive layer, and an overcoating layer of an electrically insulating polymeric material. This member is utilized in an electrophotographic copying method by, for example, initially charging the member, with an electrostatic charge of a first polarity, and imagewise exposing to form an electrostatic latent image which can be subsequently developed to form a visible image. Prior to each succeeding imaging cycle, the imaging member can be charged with an electrostatic charge of a second polarity, which is opposite in polarity to the first polarity. Sufficient additional charges of the second polarity are applied so as to create across the member a net electrical field of the second polarity. Simultaneously, mobile charges of the first polarity are created in the photoconductive layer such as by applying an electrical potential to the conductive substrate. The imaging potential which is developed to form the visible image, is present across the photoconductive layer and the overcoating layer.

There is also disclosed in Belgium Pat. No. 763,540, an electrophotographic member having at least two electrically operative layers, the first layer comprising a photoconductive layer which is capable of photogenerating charge carriers, and injecting the carriers into a continuous active layer containing an organic transporting material which is substantially non-absorbing in the spectral region of intended use, but which is active in that it allows the injection of photogenerated holes from the photoconductive layer and allows these holes to be transported through the active layer. Additionally, there is disclosed in U.S. Pat. No. 3,041,116, a photoconductive material containing a transparent plastic material overcoated on a layer of vitreous selenium contained on a substrate.

Furthermore, there is disclosed in U.S. Pat. Nos. 4,232,102 and 4,233,383, photoresponsive imaging members comprised of trigonal selenium doped with sodium carbonate, sodium selenite, and trigonal selenium doped with barium carbonate, and barium selenite or mixtures thereof.

Additionally, the use of certain squaraine pigments in photoresponsive imaging devices is known, reference, for example, the disclosure contained in a co-pending application wherein there is described an improved photoresponsive device containing a substrate, a hole blocking layer, an optional adhesive interface layer, an inorganic photogenerating layer, a photoconductive composition capable of enhancing or reducing the intrinsic properties of the photogenerating layer, and a hole transport layer. As photoconductive compositions for this device there can be selected various squaraine pigments, including hydroxy squaraine compositions of the formula as outlined on page 13, beginning at line 21 of the co-pending application. Moreover, there is disclosed in U.S. Pat. No. 3,824,099, certain photosensitive hydroxy squaraine compositions. According to the disclosure of this patent the squaraine compositions are photosensitive in normal electrostatographic imaging systems.

Also, there is disclosed in another copending application. U.S. Ser. No. 493114/83, the disclosure of which is totally incorporated herein by reference, titled Photoconductive Devices Containing Novel Squaraine Compositions, photoresponsive devices containing novel squaraine compositions of matter, such as bis-9-(8-hydroxyjulolidinyl)squaraine. As disclosed in this copending application, one photoresponsive device is comprised of a supporting substrate, a hole blocking layer, an optional adhesive interface layer, an inorganic photogenerating layer, a photoconducting composition layer capable of enhancing or reducing the intrinsic properties of the photogenerating layer, which composition is comprised of the novel squaraine materials disclosed in the copending application, and a hole transport layer. There is also illustrated in the copending application an improved photoresponsive device comprised of a substrate, a hole blocking layer, an optional adhesive or adhesion interface layer, a photoconductive composition capable of enhancing or reducing the intrinsic properties of a photogenerating layer in the infrared and/or visible range of the spectrum, which composition is comprised of the squaraine materials disclosed therein, an inorganic photogenerating layer, and a hole transport layer.

While photoresponsive devices containing the above-described squaraine compositions may be suitable for their intended purposes, there continues to be a need for the development of improved devices, particularly layered devices, containing other novel squaraine materials. Additionally, their continues to be a need for a development of a novel class of infrared squaraine photogenerating materials possessing desirable sensitivity, low dark decay, high charge acceptance values, and wherein devices containing such squaraines can be used for a number of imaging cycles in a xerographic imaging apparatus. Further, there continues to be a need for novel squaraine compositions which, when selected for layered photoresponsive imaging devices, allow the generation of acceptable images, and wherein such devices can be repeatedly used in a number of imaging cycles without deterioration thereof from the machine environment or surrounding conditions. Moreover, there continues to be a need for improved layered imaging members wherein the materials selected for the respective layers are substantially inert to users of such devices. Furthermore, there continues to be a need for overcoated photoresponsive devices which are sensitive to a broad range of wavelengths, and more specifically are sensitive to infrared light, and visible light, thereby allowing such devices to be useful in a number of imaging and printing systems wherein lasers are selected, such as gallium arsenide aluminum lasers. Also, there continues to be a need for new squaraine compositions, and processes for preparing such compositions which are simple and economically attractive. There also continues to be a need for novel squaraine compositions which when incorporated into photoreceptor devices exhibit low dark decay, and wherein the squaraine compositions selected are capable of functioning with hole and electron transporting compounds.

SUMMARY OF THE INVENTION

It is thus an object of the present invention to provide novel squaraine compositions of matter, and processes for preparing such compositions.

It is another an object of the present invention to provide improved photoresponsive imaging members containing novel squaraine compositions.

It is yet another object of the present invention to provide improved photoresponsive devices which are panchromatic, and thus sensitive to visible light as well as infrared light.

A further specific object of the present invention is the provision of an improved overcoated photoresponsive device containing a photoconductive layer comprised of novel squaraine photosensitive pigments, and a hole transport layer.

It is yet another object of the present invention to provide an improved overcoated photoresponsive device containing a hole transport layer and coated thereover a photoconductive layer containing novel squaraine compositions.

In yet another object of the present invention, there is provided a photoresponsive device containing a photoconductive composition comprised of novel squaraine compositions situated between a hole transport layer, and a photogenerating layer.

It is yet another object of the present invention to provide an improved layer overcoated photoresponsive device containing a novel squaraine photoconductive composition situated between a photogenerating layer, and the supporting substrate of such a device.

Another object of the present invention resides in the provision of an improved overcoated photoresponsive device containing a photogenerating composition situated between a hole transport layer and a photoconductive layer comprised of novel squaraine compositions, which device is simultaneously responsive to infrared light and visible light.

Another object of the present invention resides in the provision of an improved overcoated photoresponsive device containing a photoconductive layer comprised of the novel squaraine compositions described herein, situated between a hole transport layer, and a layer comprised of a photogenerating composition, which device is simultaneously responsive to infrared light and visible light.

In yet another embodiment of the present invention, there are provided imaging and printing methods with the improved overcoated photoresponsive devices described herein.

In still another object of the present invention, there are provided a novel class of infrared sensitive squaraine compositions with desirable photosensitivity, low dark decay, and high charge acceptance.

These and other objects of the present invention are accomplished by the provision of novel squaraine compositions of matter and photoresponsive devices containing such compositions. The novel squaraine compositions are of the following formula:

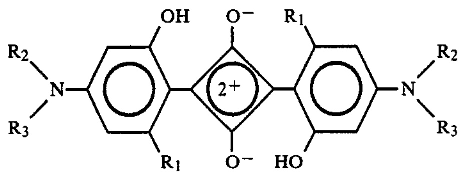

wherein $R_1$, $R_2$, and $R_3$ are independently selected from the group consisting of alkyl substituents and aryl substituents.

Examples of alkyl groups include those containing of from about 1 to about 20 carbon atoms, and preferably from 1 to 7 carbon atoms, including methyl, ethyl, propyl, butyl, hexyl, heptyl, octyl, nonyl, pentyl, and the like, with methyl, ethyl, propyl and butyl being preferred. Moreover, the alkyl groups can be substituted with other substituents providing that the objectives of the present invention are achieved, these substituents including, for example, halogen, aryl, nitro, and the like. Each of the R substituents can be comprised of identical alkyl groups, or each of the R substituents may be different alkyl groups. Thus, for example, $R_1$ on the first ring structure may be a methyl group, while $R_1$ on the second ring structure is butyl. Likewise, $R_2$ or $R_3$ on the first ring structure may be methyl and propyl, respectively, while $R_2$ an $R_3$ on the second ring structure may be methyl and butyl, respectively. Additionally, all of the R groupings can be the alkyl group methyl, propyl or butyl, for example.

Illustrative examples of aryl groups include those containing from about 6 to about 24 carbon atoms, such as phenyl, naphthyl, anthracyl, and the like, with phenyl being preferred. Additionally, the aryl groups can be substituted with substituents such as alkyl as defined herein, halogen, and the like. As is the situation with the alkyl substituents, the aryl groups can be comprised of the same substituents, thus $R_1$ on the first ring structure can be phenyl, and $R_1$ on the second ring structure can also be the phenyl group. Similarily, $R_2$ and $R_3$ on the first ring structure can be a phenyl group, while $R_2$ and $R_3$ on the second ring structure are also phenyl substituents. Also, $R_1$ on the first ring structure may be a phenyl substituent, while $R_1$ on the second ring structure is a napthyl substituent.

Illustrative specific examples of novel squaraine compositions of the present invention included within the formula illustrated herein are bis(4-dimethylamino-2-hydroxy-6-methyl-phenyl)squaraine, bis(4-dibutylamino-2-hydroxy-6-methylphenyl)squaraine, bis(4-diethylamino-2-hydroxy-6-methylphenyl)-squaraine, bis(4-ethylmethylamino-2-hydroxy-6-methylphenyl)squaraine, bis(4-dimethylamino-2-ethyl-6-hydroxyphenyl)squaraine, bis(6-carboxy-4-dimethylamino-2-hydroxyphenyl squaraine; bis(6-carboxy-4-ethylmethylamino-2-hydroxyphenyl)squaraine, bis(4-dimethylamino-2-hydroxy-6-fluorophenyl)squaraine, bis(4-ethylmethylamino-2-hydroxy-6-fluorophenyl)-squaraine, bis(2-chloro-4-dimethylamino-6-hydroxyphenyl)squaraine, and bis(2-chloro-4-ethylmethylamino-6-hydroxyphenyl)squaraine.

The novel squaraine compositions illustrated herein are generally prepared by the reaction of squaric acid and an aromatic amine. More specifically, the novel squaraine compositions of the present invention are generally prepared by suspending squaric acid in an alcohol such as n-butanol, and toluene, followed by heating. Subsequently, there is then added to the resulting mixture an aromatic amine such as dialkylaminomethylphenol.

In one illustrative embodiment, the novel squaraine compositions of the present invention are prepared by the reaction of squaric acid and an aromatic amine, in a molar ratio of from about 1:1 to about 1:4, and preferably in a ratio of from about 1 to about 2, in the presence of a mixture of an aliphatic alcohol or a phenol, and an optional azeotropic cosolvent. About 100 milliliters of alcohol per 0.2 moles of squaric acid are used, however, up to 500 milliliters of alcohol per 0.2 moles of squaric acid can be selected. Also, from about 40 milliliters to about 4,000 milliliters of azeotropic material are selected. The reaction is generally accomplished at a temperature of from about 50° C. to about 130° C. and preferably at a temperature of about 105° C. with stirring until the reaction is completed. Subsequently, the desired product is isolated from the reaction mixture by known techniques such as filtration, and identified by analytical tools including NMR, mass spectroscopy, and elemental analysis for carbon, hydrogen, and nitrogen.

Examples of amine reactants include 3-dimethylamino-5-methylphenol, 3-dibutylamino-5-methylphenol, 3-diethylamino-5-methylphenol, 3-ethylmethylamino-5-methylphenol, 3-dimethylamino-5-ethylphenol, 5-dimethylamino-3-hydroxybenzoic acid, 5-ethylmethylamino-3-hydroxybenzoic acid, 3-dimethylamino-5-fluorophenol, 3-ethylmethylamino-5-fluorophenol, 3-dimethylamino-5-chlorophenol, 3-ethylmethylamino-5-chlorophenol, and the like.

While most of the amine reactants are commercially available or reported in the literature, others may be novel precursor compositions of matter, such as the aromatic amine reactant 3-butylamino-5-methylphenol. These amines are generally prepared by reacting an appropriately substituted resorcinol, such as orcinol with a secondary amine such as dimethylamine in a molar ratio of from about 1:1 to about 1:5. About one mole of water per mole of substituted resorcinol was used. Subsequently, the resorcinol and amine are heated to a temperature of about 150° C. to 200° C. in a pressure apparatus, for about 2 to about 6 hours. Any unreacted secondary amine was removed by known methods, such as evaporation, distillation or solvent extraction, and the resulting substituted aniline product was isolated by known distillation or chromatography techniques. The precursor product was then identified by analytical tools including nuclear magnetic resonance, mass spectroscopy and infrared spectroscopy.

Illustrative examples of aliphatic alcohols selected for the preparation of the novel squaraines of the present invention include 1-butanol, 1-pentanol and 1-octanol, neopentanol, and heptanol, with 1-butanol being preferred, while illustrative examples of azeotropic materials that can be used include aromatic compositions such as benzene, toluene and xylene.

Numerous different layered photoresponsive devices containing the novel squaraine compositions illustrated herein can be fabricated. In one embodiment, the layered photoresponsive devices are comprised of a supporting substrate, a hole transport layer, and a photoconductive layer, comprised of the novel squaraines illustrated herein, situated between the supporting substrate and the hole transport layer. In another embodiment of the present invention, there is envisioned a layered photoresponsive device comprised of a substrate, a photoconductive layer comprised of the novel squaraine compositions disclosed herein, and situated between the photoconductive layer and the supporting substrate, a hole transport layer. Moreover, there is provided in accordance with the present invention an improved photoresponsive device useful in printing systems, comprised of a photoconductive composition containing the novel squaraine compositions of the present invention, which composition is situated between a photogenerating layer, and a hole transport layer, or wherein the photoconductive novel squaraine composition layer is situated between a photogenerating layer and the supporting substrate of such a device. In the latter devices, the squaraine photoconductive layer serves to enhance or reduce the intrinsic properties of the photogenerating layer in the infrared and/or visible region of the spectrum.

In one specific illustrative embodiment, the improved photoresponsive device of the present invention is comprised in the order stated of (1) a supporting substrate, (2) a hole blocking layer, (3), an optical adhesive interface layer, (4) an inorganic photogenerator layer, (5) a photoconducting composition layer capable of enhancing or reducing the intrinsic properties of the photogenerating layer, which composition is comprised of the novel squaraine materials described herein, and (6) a hole transport layer. In one important illustrative embodiment the photoresponsive device is comprised of a conductive supporting substrate, a hole blocking metal oxide layer in contact therewith, an adhesive layer, an inorganic photogenerating material overcoated on the adhesive layer, a photoconducting composition capable of enhancing or reducing the intrinsic properties of the photogenerating layer in the infrared and/or visible range of the spectrum, which composition is comprised of the novel squaraine compositions disclosed herein, and as a top layer, a hole transport layer comprised of certain diamines dispersed in a resinous matrix. The photoconductive layer composition when in contact with the hole transport layer is capable of allowing holes generated by the photogenerating layer to be transported. Further the photoconductive layer should not substantially trap holes generated in the photogenerating layer. Also, the photoconductive composition can function as a selective filter, allowing light of a certain wavelength to penetrate the photogenerating layer.

In another important embodiment, the present invention is directed to an improved photoresponsive device as described hereinbefore, with the exception that the photoconductive composition capable of enhancing or reducing the intrinsic properties of the photogenerating layer is situated between the photogenerating layer and the supporting substrate contained in the device. Accordingly, in this variation, the photoresponsive device of the present invention is comprised in the order stated of (1) a substrate, (2) a hole blocking layer, (3) an optional adhesive or adhesion interface layer, (4) a photoconductive composition capable of enhancing or reducing the intrinsic properties of a photogenerating layer in the infrared and/or visible range of the spectrum, which composition is comprised of the novel squaraine materials disclosed herein, (5) an inorganic photogenerating layer, and (6) a hole transport layer.

Exposure to illumination and erasure of the layered photoresponsive devices of the present invention may be accomplished from the front side, the rear side or combinations thereof.

The improved photoresponsive devices of the present invention can be prepared by a number of known methods, the process parameters and the order of coating of the layers being dependent on the device desired. Thus, for example, a three layered photoresponsive device can be prepared by vacuum sublimation of the photoconducting layer on a supporting substrate, and subsequently depositing by solution coating the hole transport layer. In another process variant, the layered photoresponsive device can be prepared by providing the conductive substrate containing a hole blocking layer and an optional adhesive layer, and applying thereto by solvent coating processes, laminating processes, or other methods, a photogenerating layer, a photoconductive composition comprised of the novel squaraines of the present invention, which squaraines are capable of enhancing or reducing the intrinsic properties of the photogenerating layer in the infrared and/or visible range of the spectrum, and a hole transport layer.

The improved photoresponsive devices of the present invention can be incorporated into various imaging systems, such as those conventionally known as xerographic imaging processes. Additionally, the improved photoresponsive devices of the present invention containing an inorganic photogenerating layer, and a photoconducting layer comprised of the novel squaraines of the present invention can function simultaneously in imaging and printing systems with visible light and/or infrared light. In this embodiment, the improved photoresponsive devices of the present invention may be negatively charged, exposed to light in a wavelength of from about 400 to about 1,000 nanometers, either sequentially or simultaneously, followed by developing the resulting image and transferring to paper. The above sequence may be repeated many times.

BRIEF DESCRIPTION OF THE DRAWINGS

For a better understanding of the present invention and further features thereof, reference is made to the following detailed description of various preferred embodiments wherein.

DESCRIPTION OF THE PREFERRED EMBODIMENTS

Figure 1:
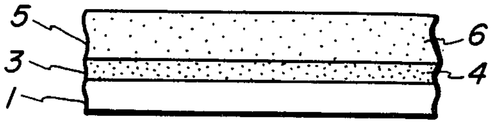
FIG. 1 is a partially schematic cross-sectional view of the photoresponsive device of the present invention.

Illustrated in FIG. 1 is a photoresponsive device of the present invention comprised of a substrate 1, a photoconductive layer 3, comprised of the novel squaraine compositions illustrated herein, particularly bis(4-dimethylamino-2-hydroxy-6-methylphenyl)squaraine, optionally dispersed in a resinous binder composition 4, and a charge carrier hole transport layer 5, dispersed in an inactive resinous binder composition 6.

Figure 2:
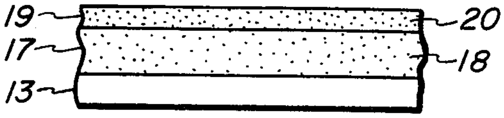
FIG. 2 is a partially schematic cross-sectional view of the photoresponsive device of the present invention.

Illustrated in FIG. 2 is essentially the same device as illustrated in FIG. 1, with the exception that the hole transport layer is situated between the supporting substrate and the photoconductive layer. More specifically with reference to this Figure, there is illustrated a photoresponsive device comprised of a supporting substrate 15, a hole transport layer 17, comprised of a hole transport composition, dispersed in an inert resinous binder composition 18, and a photoconductive layer 19, comprised of the novel squaraine compositions of the present invention, optionally dispersed in a resinous binder composition 20.

Figure 3:
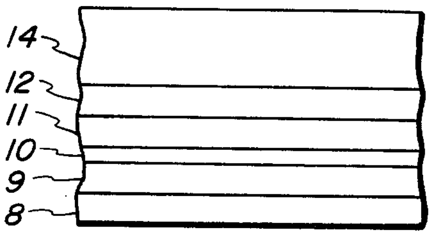
FIGS. 3 and 4 are partially schematic cross-sectional views of photoresponsive devices embraced by the present invention.

Illustrated in FIG. 3 is an improved photoresponsive device of the present invention, comprised of a substrate 8, a hole blocking metal oxide layer 9, an optional adhesive layer 10, a charge carrier inorganic photogenerating layer 11, an organic photoconductive composition layer 12 comprised of the novel squaraine compositions, and capable of enhancing or reducing the intrinsic properties of the photogenerating layer 11 in the infrared and/or visible range of the spectrum, and a charge carrier, or hole transport layer 14.

Figure 4:
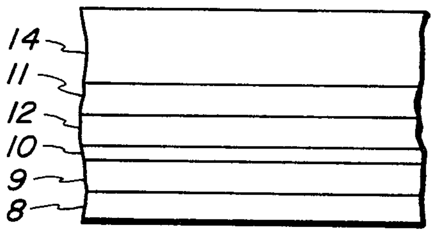

Illustrated in FIG. 4 is essentially the same device as illustrated in FIG. 3 with the exception that the photoconductive layer 12 is situated between the inorganic photogenerating layer 11 and the substrate 8, and more specifically, the photoconductive layer 12 in this embodiment is specifically situated between the optional adhesive layer 10 and the inorganic photogenerating layer 11.

Figure 5:
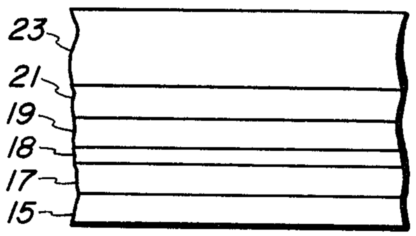
FIG. 5 is a partially schematic cross-sectional view of a photoresponsive device of the present invention.

Illustrated in FIG. 5 is one preferred photoresponsive device of the present invention, wherein the substrate 15 is comprised of Mylar in a thickness of 3 mils, containing thereover a layer of 20 percent transmissive aluminum in a thickness of about 100 Angstroms, a metal oxide layer 17 comprised of aluminum oxide in a thickness of about 20 Angstroms, a polyester adhesive layer 18, commercially available from E. I. duPont as 49,000 polyester, this layer being in a thickness of 0.05 microns, layer 19, comprised of 10 volume percent of $Na_2Se_3O$ and $Na_2CO_3$ doped trigonal selenium, in a polyvinylcarbazole binder, 90 volume percent, a photoconductive layer 21, in a thickness of about 0.5 microns, and comprised of 30 volume percent of bis(4-dimethylamino-2-hydroxy-6-methylphenyl)squaraine, dispersed in the resinous binder Formvar, commercially available from Monsanto Chemical Company 70 volume percent and a hole transport layer 23, in a thickness of about 25 microns, comprised of 50 weight percent of N,N'-diphenyl-N,N'-bis(3-methylphenyl)-[1,1'-biphenyl]-4,4'-diamine, dispersed in a polycarbonate resinous binder.

Figure 6:
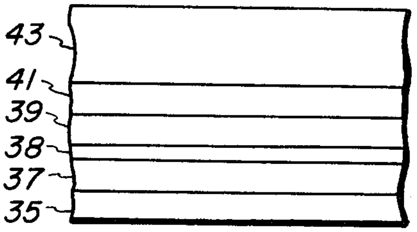
FIG. 6 illustrates another embodiment of the photoresponsive device of the present invention.

Illustrated in FIG. 6 is a further embodiment of the photoresponsive device of the present invention wherein the substrate 35 is comprised of Mylar in a thickness of 3 mils, containing about a 100 Angstrom layer of 20 percent transmissive aluminum, the metal oxide hole blocking layer 37 is aluminum oxide in a thickness of about 20 Angstroms, the optional adhesive layer 38 is a polyester material commercially available from E. I. duPont as 49,000 polyester, this layer being in a thickness of 0.05 microns, the photogenerating layer 39 is comprised of 33 volume percent of trigonal selenium dispersed in a phenoxy resinous binder, commercially available as poly(hydroxyether) Bakelite from Allied Chemical Corporation, this layer having a thickness of 0.4 microns, a photoconductive layer 41, comprised of 30 percent by volume of bis(4-dimethylamino-2-hydroxy-6-methylphenyl)squaraine dispersed in a resinous binder, commercially available as Formvar ® from Monsanto Chemical Company, 70 percent by volume, which layer has a thickness of about 0.5 microns and a hole transport layer 43 in a thickness of about 25 microns, comprised of 50 percent by weight of N,N'-diphenyl-N,N'-bis(3-methylphenyl)-[1,1'-biphenyl]-4,4'-diamine, dispersed in a polycarbonate resinous binder, 50 percent by weight.

Figure 7:
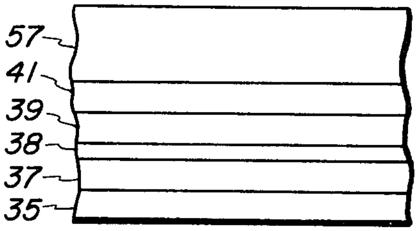
FIG. 7 illustrates another embodiment of the photoresponsive device of the present invention.

Illustrated in FIG. 7 is a further photoresponsive device of the present invention, substantially equivalent to the device as described in reference to FIG. 6, with the exception that the amine hole transporting material is replaced with an electron transporting substance.

Figure 8:
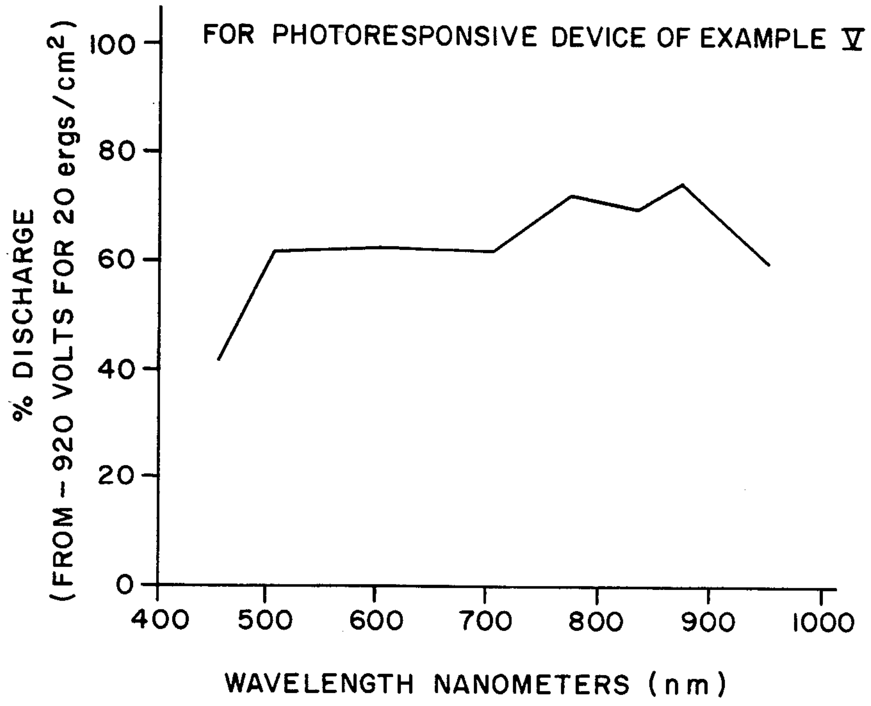
FIG. 8 illustrates the percent discharge as a function of wavelength for the photoresponsive device prepared in accordance with Example V.

In FIG. 8 there is presented a line graph generated for the photoresponsive device as prepared in Example V. As shown the photoresponsive device of Example V has a desirable discharge percentage of from about 40 to about 75 for a wavelength region of from less than about 500 nanometers to about 900 nanometers, indicating photoresponsiveness in both the visible, and infrared region of the spectrum. The percent discharge was obtained as described for example in copending application U.S. Ser. No. 493,113/83, titled Novel Squaraine Compositions, the disclosure of which is totally incorporated herein by reference.

Although not specifically illustrated with reference to FIG. 3, nor with references to FIGS. 4–6, the inorganic photogenerating layer, the organic photoconductive layer, and the charge carrier hole transport layer, are comprised of the respective compositions generally dispersed in resinous binder compositions. Thus, for example, the inorganic photogenerating layer, is comprised of an inorganic photogenerating composition as illustrated herein, dispersed in an inactive resinous binder.

The substrate layers may be opaque or substantially transparent, and may comprise any suitable material having the requisite mechanical properties. Thus the substrate may comprise a layer of insulating material such as an inorganic or organic polymeric material, such as Mylar a commercially available polymer; a layer of an organic or inorganic material having a semiconductive surface layer such as indium tin oxide, or aluminum arranged thereon, or a conductive material such as, for example, aluminum, chromium, nickel, brass or the like. The substrate may be flexible or rigid and many have a number of many different configurations, such as, for example, a plate, a cylindrical drum, a scroll, an endless flexible belt and the like. Preferably, the substrate is in the form of an endless flexible belt. In some situations, it may be desirable to coat on the back of the substrate, particularly when the substrate is an organic polymeric material, an anti-curl layer, such as for example, polycarbonate materials commercially available as Makrolon.

The thickness of the substrate layer depends on many factors, including economical considerations, thus this layer may be of substantial thickness, for example, over 100 mils, or of minimum thickness, providing there are no adverse effects on the system. In one preferred embodiment the thickness of this layer ranges from about 3 mils to about 10 mils.

The hole blocking metal oxide layers can be comprised of various suitable known materials including aluminum oxide, and the like. The preferred metal oxide layer is aluminum oxide. The primary purpose of this layer is to provide hole blocking, that is to prevent hole injection from the substrate during and after charging. Typically, this layer is of a thickness of less than 50 Angstroms.

The adhesive layers are typically comprised of a polymeric material, including polyesters, polyvinyl butyral, polyvinyl pyrrolidone and the like. Typically, this layer is of a thickness of less than about 0.3 microns.

The inorganic photogenerating layer can be comprised of known photoconductive charge carrier generating materials sensitive to visible light, such as amorphous selenium, amorphous selenium alloys, halogen doped amorphous selenium, halogen doped amorphous selenium alloys, trigonal selenium, mixtures of Groups IA and IIA elements, selenite and carbonates with trigonal selenium, reference U.S. Pat. Nos. 4,232,102 and 4,233,283, cadmium sulfide, cadmiun selenide, cadmium telluride, cadmium sulfur selenide, cadmiun sulfur telluride, cadmium seleno telluride, copper, and chlorine doped cadmium sulfide, cadmium selenide and cadmium sulfur selenide and the like. Alloys of selenium included within the scope of the present invention include selenium tellurium alloys, selenium arsenic alloys, selenium tellurium arsenic alloys, and preferably such alloys containing a halogen material such as chlorine in an amount of from about 50 to about 200 parts per million.

This layer typically has a thickness of from about 0.05 microns to about 10 microns or more, and preferably from about 0.4 microns to about 3 microns, however, the thickness of this layer is primarily dependent on the photoconductive volume loading, which may vary from 5 to 100 volume percent. Generally, it is desirable to provide this layer in a thickness which is sufficient to absorb about 90 percent or more of the incident radiation which is directed upon it in the imagewise or printing exposure step. The maximum thickness of this layer is dependent primarily upon factors such as mechanical considerations, for example whether a flexible photoresponsive device is desired.

A very important layer of the photoresponsive device of the present invention especially with respect to FIGS. 3-7 is the photoconductive layer comprised of the novel squaraine compositions disclosed herein. These compositions are generally electronically compatible with the charge carrier transport layer, in order that photoexcited charge carriers can be injected into the transport layer, and further in order that charge carriers can travel in both directions across the interface between the photoconductive layer and the charge transport layer.

Generally, the thickness of the photoconductive layer depends on a number of factors including the thicknesses of the other layers, and the percent mixture of photoconductive material contain in this layer. Accordingly, this layer can range in thickness of from about 0.05 microns to about 10 microns when the photoconductive squaraine composition is present in an amount of from about 5 percent to about 100 percent by volume, and preferably this layer ranges in thickness of from about 0.25 microns to about 1 micron, when the photoconductive squaraine composition is present in this layer in an amount of 30 percent by volume. The maximum thickness of this layer is dependent primarily upon factors such as mechanical considerations, for example whether a flexible photoresponsive device is desired.

The inorganic photogenerating materials or the photoconductive materials can comprise 100 percent of the respective layers, or these materials can be dispersed in various suitable inorganic or resinous polymer binder materials, in amounts of from about 5 percent by volume to about 95 percent by volume, and preferably in amounts of from about 25 percent by volume to about 75 percent by volume. Illustrative examples of polymeric binder resinous materials that can be selected include those as disclosed, for example, in U.S. Pat. No. 3,121,006, the disclosure of which is totally incorporated herein by reference, polyesters, polyvinyl butyral, Formvar ®, polycarbonate resins, polyvinyl carbazole, epoxy resins, phenoxy resins, especially the commercially available poly(hydroxyether) resins, and the like.

In one embodiment of the present invention, the charge carrier transport material, such as the diamine described hereinafter, may be incorporated into the photogenerating layer, or the photoconductive layer in amounts, for example, ranging from about zero volume percent to 60 volume percent.

The charge carrier transport layers, such as layer 14, can be comprised of a number of suitable materials which are capable of transporting holes, this layer generally having a thickness in the range of from about 5 microns to about 50 microns, and preferably from about 20 microns to about 40 microns. In a preferred embodiment, this transport layer comprises molecules of the formula:

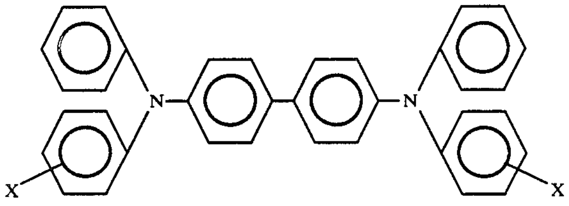

dispersed in a highly insulating and transparent organic resinous binder wherein X is selected from the group consisting of (ortho) $CH_3$, (meta) $CH_3$, (para) $CH_3$, (ortho) Cl, (meta) Cl, (para) Cl. The highly insulating resin, which has a resistivity of at least $10^{12}$ ohm-cm to prevent undue dark decay, is a material which is not necessarily capable of supporting the injection of holes from the photogenerating layer, and is not capable of allowing the transport of these holes through the material. However, the resin becomes electrically active when it contains from about 10 to 75 weight percent of the substituted N,N,N',N'-tetraphenyl[1,1-biphenyl]4-4'-diamines corresponding to the foregoing formula.

Compounds corresponding to the above formula include, for example, N,N'-diphenyl-N,N'-bis(alkylphenyl)-[1,1-biphenyl]-4,4'-diamine wherein the alkyl is selected from the group consisting of methyl such as 2-methyl, 3-methyl and 4-methyl, ethyl, propyl, butyl, hexyl and the like. With chloro substitution, the amine is N,N'-diphenyl-N,N'-bis(halo phenyl)-[1,1'-biphenyl]-4,4'-diamine wherein the halo atom is 2-chloro, 3-chloro or 4-chloro.

Other electrically active small molecules which can be dispersed in the electrically inactive resin to form a layer which will transport holes include, bis(4-diethylamine-2-methylphenyl)phenylmethane; 4′,4″-bis(diethylamino)-2′2″-dimethyltriphenyl methane; bis-4(diethylamino ·phenyl)phenylmethane; and 4,4′-bis(diethylamino)-2,2′-dimethyl triphenylmethane.

Providing the objectives of the present invention are achieved, other charge carrier transport molecules can be selected for layer 14.

Examples of the highly insulating and transparent resinous material or inactive binder resinous material, for the transport layers include materials such as those described in U.S. Pat. No. 3,121,006 the disclosure of which is totally incorporated herein by reference. Specific examples of organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binder materials are polycarbonate resins having a molecular weight (Mw) of from about 20,000 to about 100,000 with a molecular weight in the range of from about 50,000 to about 100,000 being particularly preferred. Generally, the resinous binder contains from about 10 to about 75 percent by weight of the active material corresponding to the foregoing formula, and preferably from about 35 percent to about 50 percent of this material.

With further reference to the three layered devices illustrated in FIGS. 1 and 2, the supporting substrate, the hole transport layer, the photoconductive layer, and the resinous binder compositions, as well as the thicknesses thereof, are as described herein. More specifically, for example, the supporting substrate layers 1 and 15 may be opaque or substantially transparent and may comprise a suitable material having the requisite mechanical properties. This substrate may comprise a layer of insulating material such as an inorganic or organic polymeric material, a layer of an organic or inorganic material having a conductive surface layer thereon, or a conductive material such as, for example, aluminum, chromium, nickel, indium, tin oxide, brass or the like. Also, there can be coated on the substrate as optional layers known hole blocking layers, such as aluminum oxide and an adhesive material, such as a polyester resin, commercially available for example from Goodyear Chemical Company. The substrate may be flexible or rigid and may have any of many different configurations, such as for example, a plate, a cylindrical drum, a scroll, an endless flexible belt and the like. Preferably, this substrate is in the form of an endless flexible belt. When in the configuration of a belt, in some instances it may be desirable to apply a coating of an adhesive layer to the selected substrate, of the device of FIG. 1, for example, subsequent to the application of a hole blocking layer, such as aluminum oxide.

With further regard to FIGS. 1 and 2, the photoconductive layers 3 and 19 respectively, are comprised of the novel squaraine compositions of the present invention, especially bis(4-dimethylamino-2-hydroxy-6-methylphenyl)squaraine, optionally dispersed in a resinous binder composition, 4 and 20. These squaraines are electronically compatible with the charge transport layer, thus allowing the photoexcited charge carriers to be injected into the transport layer, and allow charge carriers to travel in both directions across the interface between the charge transport layer and the photogenerating layer.

The photoconductive squaraine pigments of the present invention are generally dispersed in a resinous binder materials 4 or 20, such as various suitable inorganic or organic binder compositions, in amounts of from about 5 percent by volume to 95 percent by volume, and preferably in amounts of from about 25 percent by volume to about 75 percent by volume. Illustrative examples of polymeric resinous binder materials that can be selected include those as disclosed, for example, in U.S. Pat. No. 3,121,006, the disclosure of which is totally incorporated herein by reference, polyesters, polyvinylbutyral, Formvar®, polycarbonate resins, especially those commercially available as Makrolon®, polyvinyl carbazoles, epoxy resins, phenoxy resins, commercially available as poly(hydroxyether) resins, and the like.

The hole transport layers, 5, and 17, are as illustrated herein with reference to FIGS. 3 to 7.

Also included within the scope of the present invention are methods of imaging with the photoresponsive devices illustrated herein. These methods of imaging generally involve the formation of an electrostatic latent image on the imaging member, followed by developing the image with the developer composition, subsequently transferring the image to a suitable substrate and permanently affixing the image thereto. In those environments wherein the device is to be used in a printing mode, the imaging method involves the same steps with the exception that the exposure step is accomplished with a laser, device, or image bar, rather than a broad spectrum white light source. In the later embodiment a photoresponsive device is selected that is sensitive to infrared illumination.

Photoresponsive devices substantially equivalent to the devices as illustrated in FIG. 6 with the exception that there is selected an electron transporting layer are also disclosed. In this embodiment, reference FIG. 7 layer 57 rather than being comprised of an amine transport layer is comprised of an electron transporting layer having a thickness of from about 10 to about 34 microns, containing (4-butoxycarbonyl-9-fluorenylidene)-malonitrile and N,N′-diphenyl-N,N′-bis(3-methylphenyl)[1,1′-biphenyl]-4,4′-diamine dispersed in a polycarbonate resinous binder. The ratio of the malononitrile electron transporting material to the diamine compound is maintained at about 4:1, while the diamine is dispersed in the polycarbonate in an amount of from about 3.2 millimoles per gram of polymer. Other electron transporting substances can be selected for the devices such as those disclosed in co-pending application, U.S. Ser. No. 521198/83, titled Layered Photoresponsive Device, the disclosure of which is totally incorporated herein by reference.

The invention will now be described in detail with reference to specific preferred embodiments thereof, it being understood that these examples are intended to be illustrative only. The invention is not intended to be limited to the materials, conditions, or process parameters recited herein, it being noted that all parts and percentages are by weight unless otherwise indicated.

EXAMPLE I

A 300 milliliter three-necked flask, equipped with a Dean-Stark trap and reflux condenser was charged with squaric acid, 2.3 grams, 0.02 mol., 1-butanol, 110 milliliters and toluene, 120 milliliters. The reaction mixture was heated to 105° C. At a temperature of about 95° C., the squaric acid began to dissolve. When dissolution was complete, about 35 minutes, 3-dimethylamino-5-methylphenol, 6.0 grams, 0.04 mol. was added in one portion as a solid. The reaction temperature was maintained at 105° C. until the reaction was complete, 3 hours. On addition of the 3-dimethylamino-5-methylphenol, the colorless reaction mixture changed to a deep green. In 30 minutes when 0.1 milliliter of water had collected in the Dean-Stark trap, crystals began collecting at the bottom of the flask. After 3 hours 0.6 milliliters of water had collected in the Dean-Stark trap at which time the reaction was stopped by collecting the crystals on a Millipore LC 10 micron filter. The crystals were washed three times with ethyl acetate.

The metallic green crystals which had a decomposition point of 297° C., were identified as bis(4-dimethylamino-2-hydroxy-6-methylphenyl)squaraine, (5.9 grams, 77% yield) by mass spectroscopy, proton magnetic resonance, infrared and chemical analysis.

By decomposition at 297° C. is meant that the crystals discolored from green to black when achieving this temperature. Additionally, infrared analysis of the squaraine obtained indicated an absorption band at 1612 $cm^{-1}$, as a KBr pellet. The mass spectrum showed a molecular ion at 380 daltons. The proton magnetic resonance spectrum showed proton signals at 2.69, 3.12, 5.98, 6.19 and 13.35 ppm.

The product showed a visible absorption band in methylene chloride at 660 nanometers with a log of the extinction coefficient of 5.36.

Chemical Analysis for $C_{22}H_{24}N_2O_4$

| Element | Theoretical | Found |
|---|---|---|
| C | 69.46 | 70.05 |
| H | 6.36 | 6.45 |
| N | 7.36 | 7.49 |

EXAMPLE II

A 200 milliliter three-necked flask equipped with a Dean-Stark trap and a reflux condensor was charged with squaric acid, 2.8 grams, 0.025 mol., 1-butanol, 100 milliliters and toluene, 60 milliliters. The reaction was heated to 105° C. At a temperature of about 95° C. squaric acid began to dissolve. When dissolution was complete, about 35 minutes, 3-dimethylamino-5-methylphenol, 7.4 grams, 0.049 mol. was added in one portion as a powder followed by orcinol monohydrate, 2.8 grams, 0.02 mol. The reaction temperature was maintained at 105° until the reaction was complete, 4 hours. On addition of the 3-dimethylamino-5-methylphenol, the colorless reaction mixture changed to a deep green. Later as the reaction progressed the color of the reaction mixture changed from deep green to blue. In 20 minutes 0.7 milliliters of water had collected in the Dean-Stark trap. After 4 hours 1.2 milliliters had collected in the Dean-Stark trap, at which time the reaction was stopped by collecting the crystals on a Millipore LC 10 micron filter.

The resulting crystals were washed three times with ethyl acetate. There was obtained metallic green crystals, 7.16 grams, 75 percent yield, identified as bis(4-dimethylamino-2-hydroxy-6-methylphenyl)squaraine by infrared analysis and nuclear magnetic resonance analysis resulting in substantially identical data as reported in Example I.

EXAMPLE III

A 1 liter reaction flask was charged with squaric acid, 31.4 grams, 0.275 mole, orcinol 24.5 grams, 0.198 mole and 1-heptanol, 400 milliliters. The 1 liter flask was connected to a Dean-Stark trap and a vacuum pump and evacuated to 60 Torr. The reaction mixture was heated to reflux in a 140° C. oil bath. Refluxing began when the reaction mixture reached a temperature of 92° C. and 9.7 milliliters of water collected in the Dean-Stark trap over 3 hours. After 3 hours, the reaction mixture was deep blue in color and contained copious amounts of fine green crystals. The reaction mixture was filtered hot through a 10 micron Millipore LC filter and the crystals were washed 8 times with 50 milliliter portions of ethyl acetate. The dull green powder was dried under vacuum to a constant weight of 86 grams: yield 82%. These green crystals were identified as bis(4-dimethylamino-2-hydroxy-6-methylphenyl)squaraine by infrared and nuclear magnetic resonance analysis resulting is substantially identical data to those reported in Example I.

EXAMPLE IV

A 300 milliliter Parr minibomb was charged with orcinol monohydrate, 42 grams, 0.3 mole and di-n-butylamine, 128 milliliters. The bomb was sealed and heated to 200° C. At this temperature the internal pressure of the bomb was 90 pounds per square inch as registered on the gauge. After 48 hours at 200°, the bomb was cooled and the light brown syrup analyzed by thin-layer chromatography. The excess di-n-butylamine was removed by distillation at 20 Torr and the product was further purified by filtration through a silica gel column using ethyl acetate as the eluent. The product 3-dibutylamino-5-methylphenol was isolated in 61% yield: 43 grams. This material was not further characterized but used directly in the subsequent reaction.

A 300 milliliter 3-necked reaction flask equipped with a Dean-Stark trap and reflux condenser was charged with squaric acid, 10.3 grams, 0.09 mole, n-butanol, 100 milliliters and toluene, 100 milliliters. The reaction mixture was heated to 105° C. At a temperature of about 95° C., the squaric acid began to dissolve. When dissolution was complete, about 35 minutes, 3-dibutylamino-5-methylphenol, 43 grams, 0.18 mol. was added in one portion in toluene, 50 milliliters. The reaction temperature was maintained at 105° C. until the reaction was complete, 2 hours. After 2 hours 2.2 milliliters of water had collected in the Dean-Stark trap and crystals had separated from the deep purple-green solution. The reaction was stopped by cooling the reaction mixture to 80° C. and collecting the crystals on a Millipore LC 10 micron filter. The product 5.6 grams, yield 11% was identified as bis(4-dibutylamino-2-hydroxy-6-methylphenyl)squaraine by mass spectrometry, proton and carbon nuclear magnetic resonance. A further 16 grams, 30% could be recovered by concentrating the n-butanoltoluene mother liquors. The mass spectrum of bis(4-dibutylamino-2-hydroxy-6-methylphenyl)-squaraine showed a molecular ion at 548 daltons.

The carbon nuclear magnetic resonance spectrum showed peaks at 13.85, 20.26, 24.93, 30.06, 51.06, 97.77, 109.86, 111.13, 145.29, 155.54, 167.36, 174.18 and 182.61 ppm with respect to tetramethylsilane. The proton nuclear magnetic resonance spectrum on the other hand shows peaks at 1.0, 1.4, 1.6, 2.6, 3.1, 3.4, 6.0, 6.2 and 13.3 ppm with respect to tetramethylsilane.

EXAMPLE V

A photoresponsive device was prepared by providing an aluminized Mylar substrate of a thickness of 3 mils, followed by applying thereto with a multiple clearance film applicator, in a set thickness of 0.5 mils, a layer of 3-aminopropyltrimethoxysilane available from PCR Research Chemicals, Florida, in ethanol, in a 1:50 volume ratio. This layer was then allowed to dry for 5 minutes at room temperature, followed by curing for 10 minutes at 110° C. in a forced air oven. A photoconductive layer containing 30 percent by weight of bis(4-dimethylamino-2-hydroxy-6-methylphenyl)squaraine, prepared in accordance with Example I, was then formulated as follows:

In a separate 2 oz. amber bottle there was added 0.33 grams of the respective squaraine, 0.77 grams of Vitel PE-200®, a polyester available from Goodyear, 70 grams of ⅛" stainless steel shot, and 16.34 grams of methyl ethyl ketone/toluene solvent mixture, in a 4:1 volume ratio. The above mixture was placed on a ball mill for 24 hours. The resulting slurry was then coated on the substrate with a multiple clearance film applicator, to a wet thickness of 1 mil. The layers were allowed to air dry for 5 minutes. The resulting device was dried at 135° C. for 6 minutes in a forced air oven. The dry thickness of the squaraine layer was 1 micron.

The above photoconductive layer was then overcoated with a charge transport layer, which was prepared as follows:

A transport layer composed of 50 percent by weight Makrolon®, a polycarbonate resin available from Larbensabricken Bayer A.G., was mixed with 50 percent by weight N,N'-diphenyl-N,N'-bis(3-methylphenyl)-1,1'-biphenyl-4,4'-diamine. This solution was mixed to 9 percent by weight in methylene chloride. All of these components were placed in an amber bottle and dissolved. The mixture was coated to give a layer with a dry thickness of 30 microns on top of the above photoconductive layer, using a multiple clearance film applicator (15 mils wet gap thickness). The resulting device was then air dried at room temperature for 20 minutes and then in a forced air oven at 135° C. for 6 minutes.

EXAMPLE VI

A photoresponsive device was prepared by providing an aluminized Mylar substrate of a thickness of 3 mils, followed by applying thereto with a multiple clearance film applicator, in a wet thickness of 0.5 mils, a layer of 3-aminopropyltrimethoxysilane available from PCR Research Chemicals, Florida, in ethanol, in a 1:50 volume ratio. This layer was then allowed to dry for 5 minutes at room temperature, followed by curing for 10 minutes at 110° C. in a forced air oven. A photoconductive layer containing 30 percent by weight of bis(4-dimethylamino-2-hydroxy-6-methylphenyl)squaraine, prepared in accordance with Example II, was then formulated as follows:

In a separate 2 oz. amber bottle there was added 0.33 grams of the respective squaraine, 0.33 grams of Vitel PE-200®, a polyester available from Goodyear, 70 grams of ⅛" stainless steel shot, and 16.34 grams of methyl ethyl ketone/toluene solvent mixture, in a 4:1 volume ratio. The above mixture was placed on a ball mill for 24 hours, the resulting slurry was then coated on the substrate with a multiple clearance film applicator, to a wet thickness of 1.5 mil. The layer was allowed to air dry for 5 minutes. The resulting device was dried at 135° C. for 6 minutes in a forced air oven. The dry thickness of the squaraine layer was 1.4 micron.

The above photoconductive layer was then overcoated with a charge transport layer, which was prepared as follows:

A transport layer composed of 50 percent by weight Makrolon®, a polycarbonate resin available from Larbensabricken Bayer A.G., was mixed with 50 percent by weight N,N'-diphenyl-N,N'-bis(3-methylphenyl)-1,1'-biphenyl-4,4'-diamine. This solution was mixed to 9 percent by weight in methylene chloride. All of these components were placed in an amber bottle and dissolved. The mixture was coated to give a layer with a dry thickness of 30 microns on top of the above photoconductive layer, using a multiple clearance film applicator (15 mils wet gap thickness). The resulting device was then air dried at room temperature for 20 minutes and then in a forced air oven at 135° C. for 6 minutes.

EXAMPLE VII

A photoresponsive device was prepared by providing an aluminized Mylar substrate of a thickness of 3 mils, followed by applying thereto with a multiple clearance film applicator, in a wet thickness of 0.5 mils, a layer of 3-aminopropyltrimethoxysilane available from PCR Research Chemicals, Florida, in ethanol, in a 1:50 volume ratio. This layer was then allowed to dry for 5 minutes at room temperature, followed by curing for 10 minutes at 110° C. in a forced air oven. A photoconductive layer containing 30 percent by weight of bis(4-dimethylamino-2-hydroxy-6-methylphenyl)squaraine, prepared in accordance with Example I, was then formulated as follows:

In a separate 2 oz. amber bottle there was added 0.40 grams of the respective squaraine, 0.40 grams of Vitel PE-200®, a polyester available from Goodyear, 71 grams of ⅛" stainless steel shot, and 12.86 grams of methyl ethyl ketone/toluene solvent mixture, in a 4:1 volume ratio. After the above mixture was placed on a ball mill for 24 hours, the resulting slurry was then coated on the substrate with a multiple clearance film applicator, to a wet thickness of 1 mil. The layer was allowed to air dry for 5 minutes. The resulting device was dried at 135° C. for 6 minutes in a forced air oven. The dry thickness of the squaraine layer was 1 micron.

The above photoconductive layer was then overcoated with a charge transport layer, which was prepared as follows:

A transport layer composed of 50 percent by weight Makrolon®, a polycarbonate resin available from Larbensabricken Bayer A.G., was mixed with 50 percent by weight N,N'-diphenyl-N,N'-bis(3-methylphenyl)-1,1'-biphenyl-4,4'-diamine. This solution was mixed to 9 percent by weight in methylene chloride. All of these components were placed in an amber bottle and dissolved. The mixture was coated to give a layer with a dry thickness of 30 microns on top of the above photoconductive layer, using a multiple clearance film applicator (15 mils wet gap thickness). The resulting device was then air dried at room temperature for 20 minutes and then in a forced air oven at 135° C. for 6 minutes.

EXAMPLE VIII

A photoreceptor device was prepared by providing an aluminized Mylar® substrate in a thickness of 3 mils and applying thereto in a wet thickness of 0.5 mils, a layer of 0.5 percent by weight of DuPont 49,000 adhesive, a polyester available from DuPont, in methylene chloride and 1,1,2-trichloroethane (4:1 volume ratio) with a multiple clearance film applicator. The wet thickness was 0.5 mil. This layer was then allowed to dry for one minute at room temperature and 10 minutes at 100° C. in a forced air oven. The resulting layer had a dry thickness of about 0.05 microns.

A photogenerator layer containing 33 percent by volume of trigonal selenium, and 13 percent by volume of N,N'-diphenyl-N,N'-bis(3-methylphenyl)1,1'-biphenyl-4,4'-diamine in the phenoxy binder Bakelite available from Union Carbide was prepared as follows:

In a 4 oz. amber bottle was added 1.6 grams of the above phenoxy resin. 21 milliliters methyl ethyl ketone and 7 milliliters methoxyethyl acetate. Added to this solution was 3.2 grams of trigonal selenium, and 200 grams ⅛" stainless steel shot. The above mixture was placed on a ball mill for 72–96 hours. This slurry was then coated on the above polyester with a multiple clearance film applicator, to a wet thickness of 0.5 mils. This layer was then dried at 135° C. in forced air for 6 minutes.

A photoconductive layer containing 30 percent by weight of bis(4-dimethylamino-2-hydroxy-6-methylphenyl)squaraine, prepared in accordance with Example I, was then formulated as follows:

In a separate 2 oz. amber bottle there was added 0.33 grams of the respective squaraine, 0.77 grams of Vitel PE-200, a polyester available from Goodyear, 70 grams of ⅛" stainless steel shot, and 16.34 grams of methyl ethyl ketone/toluene solvent mixture, in a 4:1 volume ratio. The above mixture was placed on a ball mill for 24 hours. The resulting slurry was then coated on the above photogenerating layer with a multiple clearance film applicator, to a wet thickness of 1 mil. The layers were allowed to air dry for 5 minutes. The resulting device was dried at 135° C. for 6 minutes in a forced air oven. The dry thickness of the squaraine layer was 1 micron.

The above photoconductive layer was then overcoated with a charge transport layer, which was prepared as follows:

A transport layer composed of 50 percent by weight Makrolon®, a polycarbonate resin available from Larbensabricken Bayer A.G., was mixed with 50 percent by weight N,N'-diphenyl-N,N'-bis(3-methylphenyl)-1,1'-biphenyl-4,4'-diamine. This solution was mixed to 9 percent by weight in methylene chloride. All of these components were placed in an amber bottle and dissolved. The mixture was coated to give a layer with a dry thickness of 30 microns on top of the above photoconductive layer, using a multiple clearance film applicator (15 mils wet gap thickness). The resulting device was then air dried at room temperature for 20 minutes and then in a forced air oven at 135° C. for 6 minutes.

EXAMPLE IX

A photoresponsive device was prepared by providing brush grained aluminum substrate of a thickness of 150 microns, followed by applying thereto with a multiple clearance film applicator, in a wet thickness of 0.5 mls, a layer of 3-aminopropyltrimethoxysilane available from PCR Research Chemicals, Florida, in ethanol, in a 1:20 volume ratio. This layer was then allowed to dry for 5 minutes at room temperature, followed by curing for 10 minutes at 110° C. in a forced air oven. A photoconductive layer containing 30 percent by weight of bis(4-dimethylamino-2-hydroxy-6-methylphenyl)-squaraine, prepared in accordance with Example II was then formulated as follows:

In a separate 2 oz. amber bottle there was added 0.33 grams of the respective squaraine, 0.77 grams of Vitel PE-200®, a polyester available from Goodyear, 70 grams of ⅛" stainless steel shot, and 12.86 grams of methyl ethyl ketone/toluene solvent mixture, in a 4:1 volume ratio. The above mixture was placed on a ball mill for 24 hours, the resulting slurry was then coated on the substrate with a multiple clearance film applicator, to a wet thickness of 1.5 mil. The layer was allowed to air dry for 5 minutes. The resulting device was dried at 135° C. for 6 minutes in a forced air oven. The dry thickness of the squaraine layer was 1.4 micron.

The above photoconductive layer was then overcoated with a charge transport layer, which was prepared as follows:

The solution for the transport layer was prepared by dissolving 1.0 gram of (4-butoxycarbonyl-9-fluorenyl)-malononitrile, 0.38 grams of N,N'-diphenyl-N,N'-bis(3-methylphenyl)-[1,1'-biphenyl]-4,4'-diamine, and 1.0 grams of Makrolon® in 20 milliliters of methylene chloride. This solution was then coated by means of a multiple clearance film applicator over the above photoconductive layer resulting in a 17 micron thick transport layer, after drying in a forced air oven at 135° C. for 30 minutes.

Each of the photoresponsive devices of Examples V to IX were then tested for photosensitivity in the visible and infrared region of the spectrum by negatively charging with a corotron to −950 volts the devices of Examples V to VIII, while the device of Example IX was positively charged with a corotron with 820 volts, followed by simulaneously exposing each device tomonochromatic light in a wavelength region of from about 400 to about 1,000 nanometers. The surface potential of each device was then measured with an electrical probe after exposure to these wavelengths. The extent of discharge, which indicates photoresponsiveness, of each device was then measured.

The devices of Examples V to IX had sufficient discharge so as to respond to light in a wavelength range of from about 400 to about 950 nanometers, indicating both visible and infrared photosensitivity for these devices.

Also the photoresponsive devices as prepared in Examples V to VIII, were tested for photosensitivity by charging each of the devices in the dark to a surface potential of 950 volts, while the device of Example IX was charged in the dark to a surface potential of 820 volts, followed by measuring with an electrical probe the amount of light energy of monochromatic light supplied by a Xenon lamp, in ergs per centimeter squared required to discharge each device to one half of its surface potential. A low discharge number, for example below 100, indicates excellent photosensitivity for the devices involved.

At wavelengths of 400 to 700 nanometers, the devices of Examples V, VI, VII, and VIII, had photodischarge numbers of 25, 18, 9, and 4 respectively, while at wavelengths of 830 nanometers the devices of Examples V, VI, VII, VIIII and IX, had photodischarge numbers of 10, 8, 5, 7, and 25 respectively.

Although the invention has been described with reference to specific preferred embodiments, it is not intended to be limited thereto, rather those skilled in the art will recognize that variations and modifications may be made therein which are within the spirit of the present invention and within the scope of the following claims.

We claim:

1. An improved photoresponsive device comprised in the order stated of (1) a supporting substrate, (2) a photoconductive layer comprised of the squaraine compositions of the following formula, and (3) a diamine hole transport layer

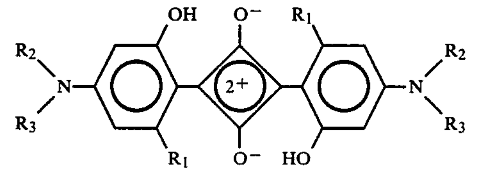

wherein $R_1$, $R_2$ and $R_3$ are independently selected from the group consisting of alkyl substituents and aryl substituents.

2. An improved photoresponsive device comprised in the order stated of (1) a supporting substrate, (2) a diamine hole transport layer, and (3) a photoconductive layer comprised of the squaraine compositions of the following formula

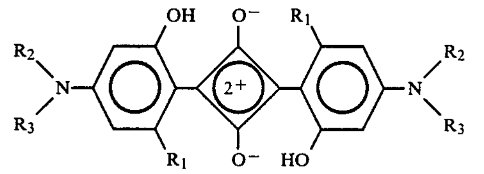

wherein $R_1$, $R_2$ and $R_3$ are independently selected from the group consisting of alkyl substituents and aryl substituents.

3. An improved photoresponsive device in accordance with claim 1 wherein the squaraine composition is bis(4-dimethylamino-2-hydroxy-6-methylphenyl)-squaraine.

4. An improved photoresponsive device in accordance with claim 2 wherein the squaraine composition is bis(4-dimethylamino-2-hydroxy-6-methylphenyl)-squaraine.

5. A photoresponsive device in accordance with claim 1 wherein the supporting substrate is comprised of a conductive metallic substance, or an insulating polymeric composition containing on its surface a semiconductive layer.

6. A photoconductive device in accordance with claim 2 wherein the supporting substrate is comprised of a conductive metallic substance, or an insulating polymeric composition containing on its surface a semiconductive layer.

7. A photoresponsive device in accordance with claim 5 wherein the substrate is aluminum, and a semiconductive material is transmissive aluminum or indium tin oxide.

8. A photoresponsive device in accordance with claim 6 wherein the conductive substrate is aluminum, and the semiconductive material is transmissive aluminum or indium tin oxide.

9. An improved photoresponsive device in accordance with claim 1 wherein the squaraine composition is dispersed in a resinous binder in an amount of from about 5 percent by volume to about 95 percent by volume, and the diamine hole transport material is dispersed in a resinous binder in an amount of from about 10 percent by weight to about 75 percent by weight.

10. An improved photoresponsive device in accordance with claim 2 wherein the squaraine composition is dispersed in a resinous binder in an amount of from about 5 percent by volume to about 95 percent by volume, and the diamine hole transport material is dispersed in a resinous binder in an amount of from about 10 percent by weight to about 75 percent by weight.

11. An improved photoresponsive device in accordance with claim 9 wherein the resinous binder for the squaraine composition is a polyester, polyvinylcarbazole, polyvinylbutyral, a polycarbonate, or a phenoxy resin, and the resinous binder for the diamine hole transport material is a polycarbonate, a polyester, or a vinyl polymer.

12. A photoresponsive device in accordance with claim 10 wherein the resinous binder for the squaraine composition is a polyester, polyvinylcarbazole, polyvinylbutyral, polycarbonate, or a phenoxy resin, and the resinous binder for the diamine hole transport material is a polycarbonate, a polyester, or vinyl polymer.

13. A photoresponsive device in accordance with claim 1 wherein the diamine composition comprises molecules of the formula:

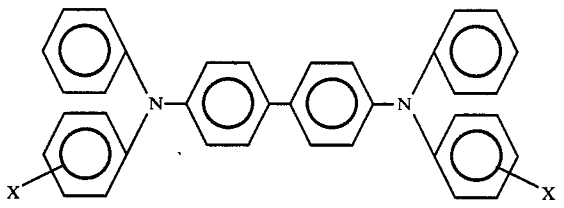

dispersed in a highly insulating and transparent organic resinous material wherein X is selected from the group consisting of ortho($CH_3$), meta($CH_3$), para($CH_3$), ortho(Cl), meta(Cl), para(Cl).

14. A photoresponsive device in accordance with claim 2 wherein the diamine composition comprises molecules of the formula:

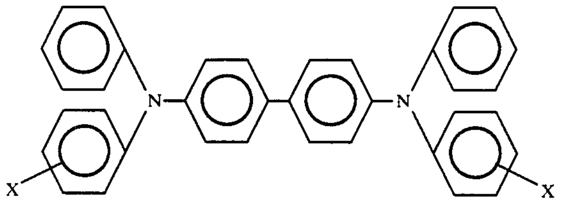

dispersed in a highly insulating and transparent organic resinous material wherein X is selected from the group consisting of ortho($CH_3$), meta($CH_3$), para($CH_3$), ortho(Cl), meta(Cl), para(Cl).

15. A photoresponsive device in accordance with claim 13 wherein the diamine is comprised of N,N'-diphenyl-N,N'-bis(3-methylphenyl)-[1,1-biphenyl]-4,4'-diamine.

16. A photoresponsive device in accordance with claim 14 wherein the diamine is comprised of N,N'-diphenyl-N,N'-bis(3-methylphenyl)-[1,1-biphenyl]-4,4'-diamine.

17. An improved photoresponsive device comprised in the order stated of the following layers, (1) a supporting substrate, (2) a metal oxide hole blocking layer, (3) an inorganic photogenerating layer, (4) a photoconductive material comprised of the squaraine compositions of the following formula, and (5) a diamine hole transport layer

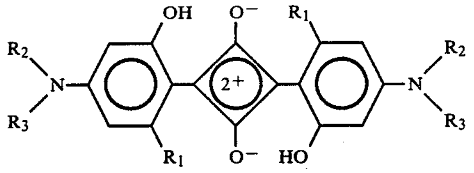

wherein $R_1$, $R_2$ and $R_3$ are independently selected from the group consisting of alkyl substituents and aryl substituents.

18. An improved photoresponsive device comprised in the order stated of the following layers, (1) a supporting substrate, (2) a metal oxide hole blocking layer, (3) a photoconductive material comprised of the squaraine compositions of the following formula, (4) an inorganic photogenerating layer, and (5) a diamine hole transport layer

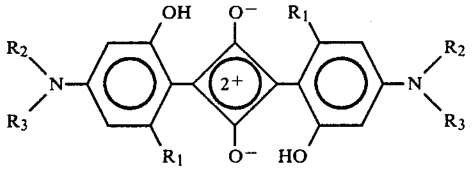

wherein $R_1$, $R_2$ and $R_3$ are independently selected from the group consisting of alkyl substituents and aryl substituents.

19. An improved photoresponsive device in accordance with claim 17 wherein the supporting substrate is comprised of a conductive metallic substance, or an insulating polymeric composition containing on its surface a semiconductive material.

20. A photoresponsive device in accordance with claim 18 wherein the supporting substrate is comprised of a conductive metallic substance, or an insulating polymeric composition containing on its surface a semiconductive material.

21. A photoresponsive device in accordance with claim 19 wherein the conductive substrate is aluminum, and the semiconductive material is transmissive aluminum, or indium tin oxide.

22. A photoresponsive device in accordance with claim 20 wherein the conductive substrate is aluminum, and the semiconductive material is transmissive aluminum, or indium tin oxide.

23. An improved photoresponsive device in accordance with claim 17 wherein the squaraine composition is dispersed in a resinous binder in an amount of from about 10 percent by weight to about 75 percent by weight and the diamine hole transport material is dispersed in a resinous binder in an amount of from about 10 percent by weight to about 75 percent by weight.

24. An improved photoresponsive device in accordance with claim 18 wherein the squaraine composition is dispersed in a resinous binder in an amount of from about 5 percent by volume to about 95 percent by volume, and the diamine hole transport material is dispersed in a resinous binder in an amount of from about 10 percent by weight to about 75 percent by weight.

25. An improved photoresponsive device in accordance with claim 23 wherein the resinous binder for the squaraine composition is a polyester, polyvinylcarbazole, polyvinylbutyral, a polycarbonate, or a phenoxy resin, and the resinous binder for the diamine hole transport material is a polycarbonate, a polyester, or a vinyl polymer.

26. An improved photoresponsive device in accordance with claim 24 wherein the resinous binder for the squaraine composition is a polyester, polyvinylcarbazole, polyvinylbutyral, a polycarbonate, or a phenoxy resin, and the resinous binder for the diamine hole transport material is a polycarbonate, a polyester, or a vinyl polymer.

27. An improved photoresponsive device in accordance with claim 17 wherein the diamine composition comprises molecules of the formula:

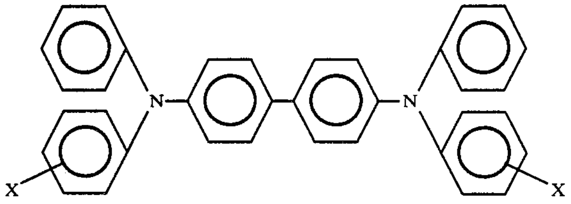

dispersed in a highly insulating and transparent organic resinous material wherein X is selected from the group consisting of ortho ($CH_3$), meta ($CH_3$), para ($CH_3$), ortho (Cl), meta (Cl), para (Cl).

28. An improved photoresponsive device in accordance with claim 18 wherein the diamine composition comprises molecules of the formula:

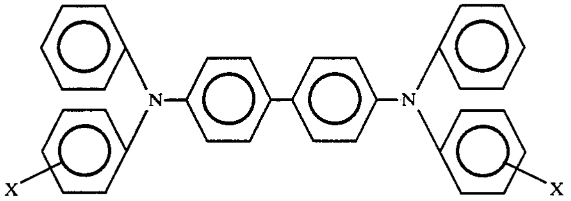

dispersed in a highly insulating and transparent organic resinous material wherein X is selected from the group consisting of ortho ($CH_3$), meta ($CH_3$), para ($CH_3$), ortho (Cl), meta (Cl), para (Cl).

29. An improved photoresponsive device in accordance with claim 27 wherein the resinous binder for the diamine hole transport material is a polycarbonate, a polyester, or a vinyl polymer.

30. An improved photoresponsive device in accordance with claim 28 wherein the resinous binder for the diamine hole transport material is a polycarbonate, a polyester, or a vinyl polymer.

31. An improved photoresponsive device in accordance with claim 27 wherein the diamine is comprised of N,N'-diphenyl-N,N'-bis(3-methylphenyl)-[1,1-biphenyl]-4,4'-diamine.

32. An improved photoresponsive device in accordance with claim 28 wherein the diamine is comprised of N,N'-diphenyl-N,N'-bis(3-methylphenyl)-[1,1-biphenyl]-4,4'-diamine.

33. An improved photoresponsive device in accordance with claim 17 wherein the photogenerating layer is selenium, a halogen doped selenium substance, selenium alloys, or halogen doped selenium alloys.

34. An improved photoresponsive device in accordance with claim 18 wherein the photogenerating layer is selenium, a halogen doped selenium substance, selenium alloys, or halogen doped selenium alloys.

35. An improved photoresponsive device in accordance with claim 33 wherein the selenium alloy is selenium tellurium, selenium arsenic, or selenium tellurium arsenic.

36. An improved photoresponsive device in accordance with claim 33 wherein the selenium alloy is selenium tellurium, selenium arsenic, or selenium tellurium arsenic.

37. An improved photoresponsive device in accordance with claim 35 wherein the selenium alloy is doped with chlorine in an amount of from about 50 parts per million to about 200 parts per million.

38. An improved photoresponsive device in accordance with claim 36 wherein the selenium alloy is doped with chlorine in an amount of from about 50 parts per million to about 200 parts per million.

39. An improved photoresponsive device in accordance with claim 17 wherein the photogenerating layer is trigonal selenium.

40. An improved photoresponsive device in accordance with claim 18 wherein the photogenerating layer is trigonal selenium.

41. An improved photoresponsive device in accordance with claim 17 wherein the photogenerating layer is trigonal selenium doped with $Na_2SeO_3$ and $Na_2CO_3$.

42. A photoresponsive device in accordance with claim 17 wherein the squaraine composition is bis(4-dimethylamino-2-hydroxy-6-methylphenyl)squaraine.

43. A photoresponsive device in accordance with claim 18 wherein the squaraine composition is bis(4-dimethylamino-2-hydroxy-6-methylphenyl)squaraine.

44. The squaraine composition bis(4-ethylmethylamino-2-hydroxy-6-methylphenyl)squaraine.

45. The squaraine composition bis(4-dimethylamino-2-ethyl-6-hydroxyphenyl)squaraine.

46. An improved photoresponsive imaging member consisting essentially of a supporting substrate, a photoconductive layer comprised of a squaraine compound of the following formula

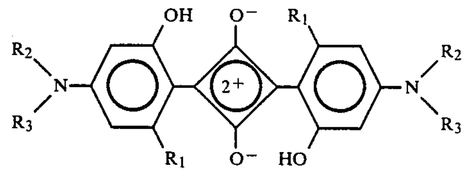

wherein $R_1$, $R_2$ and $R_3$ are independently selected from the group consisting of alkyl substituents and aryl substituents; and an aryl amine hole transport layer.

47. An improved photoresponsive imaging member in accordance with claim 46 wherein the squaraine is selected from the group consisting of bis(4-dimethylamino-2-hydroxy-6-methylphenyl)squaraine; bis(4-dibutylamino-2-hydroxy-6-methylphenyl)squaraine; and bis(4-diethylamino-2-hydroxy-6-methylphenyl)-squaraine.

48. An imaging member in accordance with claim 46 wherein the aryl amine is N,N'-diphenyl-N,N'-bis(3-methylphenyl)-[1,1-biphenyl]-4,4'-diamine.

49. An improved photoresponsive device in accordance with claim 17 further including an adhesive layer situated between the metal oxide hole blocking layer in the inorganic photogenerating layer.

50. An improved photoresponsive device in accordance with claim 18 wherein there is further included an adhesive layer situated between the metal oxide hole blocking layer and the photoconductive squaraine composition layer.

51. Squaraine compositions of the following formula:

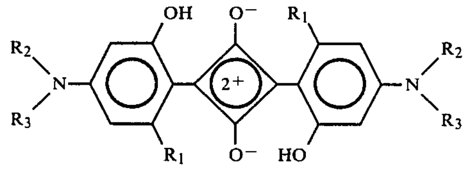

wherein $R_1$, $R_2$, and $R_3$ are independently selected from the group consisting of alkyl substituents and aryl substituents.

52. A squaraine composition in accordance with claim 51 wherein the alkyl substituents contain from about 1 carbon atom to about 20 carbon atoms.

53. A squaraine composition in accordance with claim 52 wherein the alkyl substituents are methyl, ethyl, propyl, butyl, or pentyl.

54. A squaraine composition in accordance with claim 51 wherein the aryl substituent contains from about 6 to about 24 carbon atoms.

55. A squaraine composition in accordance with claim 54 wherein the aryl substituent is phenyl.

56. A squaraine composition in accordance with claim 51 wherein $R_1$, $R_2$, and $R_3$, are alkyl substituents of from about 1 to about 10 carbon atoms.

57. A squaraine composition in accordance with claim 56 wherein the alkyl substituent is methyl.

58. A squaraine composition in accordance with claim 56 wherein the alkyl substituents are methyl.

59. The squaraine composition bis(4-dimethylamino-2-hydroxy-6-methylphenyl)squaraine.

60. The squaraine composition bis(4-dibutylamino-2-hydroxy-6-methylphenyl)squaraine.

61. The squaraine composition bis(4-diethylamino-2-hydroxy-6-methylphenyl)squaraine.

* * * * *